(12) United States Patent
Krahn et al.

(10) Patent No.: US 6,757,420 B2
(45) Date of Patent: Jun. 29, 2004

(54) INSPECTION DEVICE FOR PACKAGES

(75) Inventors: Andreas Krahn, Berlin (DE); Jürgen Saedler, Berlin (DE); Jan Schlegel, Berlin (DE); Anette Therese Lang-Schöll, München (DE); Egbert Jux, Mainaschaff (DE)

(73) Assignee: Novartis AG, Basel (CH)

( * ) Notice: Subject to any disclaimer, the term of this patent is extended or adjusted under 35 U.S.C. 154(b) by 586 days.

(21) Appl. No.: 09/746,398

(22) Filed: Dec. 21, 2000

(65) Prior Publication Data

US 2001/0016059 A1 Aug. 23, 2001

(30) Foreign Application Priority Data

Dec. 22, 1999 (EP) ............................................ 99125674

(51) Int. Cl.⁷ ................................................ G06K 9/00
(52) U.S. Cl. ................ 382/142; 250/223 B; 356/239.5; 356/435; 356/603; 356/613; 382/101; 382/143
(58) Field of Search ......................... 382/101, 142–143; 250/223 R, 223 B; 356/435, 603–613, 239.4, 233.5

(56) References Cited

U.S. PATENT DOCUMENTS

| 4,399,367 | A |   | 8/1983  | Grube et al. ............... 250/560 |
|-----------|---|---|---------|-------------------------------------|
| 4,943,713 | A | * | 7/1990  | Yoshida .................. 250/223 B |
| 5,298,977 | A | * | 3/1994  | Shintani et al. ............ 356/603 |
| 5,568,715 | A | * | 10/1996 | Ebel et al. ...................... 53/54 |
| 5,943,436 | A |   | 8/1999  | Ebel et al. ................... 382/143 |
| 5,982,493 | A | * | 11/1999 | Lehnen et al. ............... 356/613 |
| 6,023,663 | A | * | 2/2000  | Kim ............................. 702/81 |
| 6,226,126 | B1 | * | 5/2001 | Conemac .................... 359/168 |
| 6,234,648 | B1 | * | 5/2001 | Borner et al. ............... 362/235 |
| 6,250,774 | B1 | * | 6/2001 | Begemann et al. ......... 362/231 |
| 6,485,981 | B1 | * | 11/2002 | Fernandez ................... 436/71 |
| 6,582,454 | B2 | * | 6/2003 | Yayama ....................... 607/89 |

FOREIGN PATENT DOCUMENTS

| EP | 0 413 817 A1 | 5/1989 |
| EP | 0 686 563 A2 | 6/1995 |

* cited by examiner

Primary Examiner—Bhavesh M. Mehta
Assistant Examiner—Gregory Desire
(74) Attorney, Agent, or Firm—Jian S. Zhou; Rob Gorman; R. Scott Meece

(57) ABSTRACT

The invention is concerned with the problem of providing an automatic inspection device, with which it is possible to determine, with little effort and without contact, whether packages, particularly sealed blister packages consisting of a blister container and a cover film, are free of defects. This problem is solved by the use of at least two light sources, which are arranged at a certain distance from one another and each emit a light bundle at a predetermined wavelength range, whereby the emission maxima of the two light sources are offset in relation to one another. The light sources are arranged such that the packages are vertically illuminated. The light reflected by the packages is recorded by a CCD camera and the digital images are stored in a computer, so that they are available in a computer-supported image-processing and documentation system.

15 Claims, 8 Drawing Sheets

INSPECTION DEVICE FOR PACKAGES

This application claims benefit under 35 USC §119 of European patent application No. EP 99125674.4 filed Dec. 22, 1999.

The invention relates to a method and a device for detecting defects in packages, especially in blister packages.

The packages in question are frequently so-called blister packages. A blister package consists of a plastic container, for example of polypropylene (PP) and a cover film, the top of the container being sealed with the film after the moulding has been placed in the plastic container. The films employed are preferably multi-layered films. They consist of a metallic base foil, for example aluminum, a plastic film material mounted thereon, which is printed on the upper side and/or on the side facing the metal foil, and a plastic film material on the lower side, which can be sealed to a plastic container. Laminated foils of this kind are often inscribed on top with various data, such as the use-by date, a batch number and other details describing the contents of the package.

Ophthalmic mouldings are usually put away in a package for storage and for transport. In particular, contact lenses that are produced in large unit numbers, for example disposable contact lenses, are sealed into blister packages. Such contact lenses are preferably manufactured by the so-called mould or full-mould process. In this process, the lenses are manufactured into their final shape between two moulds, so that there is no need to subsequently finish the surfaces of the lenses, nor to finish the edges. The contact lenses produced in this manner are moulded parts having little mechanical stability and a water content of more than 60% by weight. After its manufacture, the lens is metrologically checked and then placed in a blister container, to which isotonic sodium chloride solution (saline) is also added. Then, the cover film is placed on several blister containers, and is sealed to the blister containers by a sealing unit, thus producing a blister strip. The package subsequently undergoes heat sterilisation at 121° C. in an autoclave. In order that a single blister package can be separated from the strip again, enabling the customer to open it, the cover film is additionally provided with perforated lines.

Optical components produced in series, e.g. contact lenses, have to be checked for defects such as scratches, shrinkage or edges that have broken away. The components recognised as defective are then rejected. However, at the present time, there is no provision for verifying whether the sealed package has defects. These defects include a defective sealing seam, which for example only makes an incomplete seal or is too narrow, or else cracks in the PP container, so that the isotonic saline can leak out and dry out the contact lens. The customer then discovers an unusable contact lens and is of course annoyed. Or, the contact lens appears to be still usable, but is no longer sterile, since bacteria was able to penetrate into the package through the broken barriers. In addition, the position of the perforations can be shifted when sealing, so that it is only possible to separate a blister package from the blister strip with great difficulty. However, if these defects are recognized by chance or by spot checks, then either the whole batch has to be rejected or all the contact lens packages have to undergo 100% manual checking. Both procedures involve substantial costs. Similar problems also arise with other packages that are filled with sensitive products.

The invention is therefore based on the problem of providing an automatic inspection device with which it is possible to determine, with little effort and without contact, whether packages, particularly sealed blister packages consisting of a blister container and a cover film, are free of defects, especially in respect of the blister containers, the sealing seam and the perforation. Furthermore, the packages recognized as defective should be automatically sorted out. In addition, an inspection device of this kind should enable a high number of units to pass through, since as a rule the goods to be packaged arrive in rapid succession.

The invention solves this problem with the features indicated in claim 1. As far as further essential refinements are concerned, reference is made to the dependent claims.

The invention solves the problem with the use of at least two light sources, which are arranged at a certain distance from one another and each emit a light bundle at a predetermined wavelength range, whereby the emission maxima of the two light sources are offset in relation to one another. The light sources are arranged such that the packages are vertically illuminated. The light reflected by the packages is recorded by a CCD camera and the digital images are stored in a computer, so that they are available in a computer-aided image-processing and documentation system. The images of different packages can be compared with one another, thus making a statistical analysis of defects possible. Moreover, a computer-controlled handling system is provided, which serves to prepare, present and further handle the blister packages. In particular, the damaged blister packages are automatically sorted out.

Further details and advantages of the invention may be seen from the description that follows and the drawing. In the drawing, FIG. 1 shows a schematic illustration of an embodiment of an inspection device according to the invention;

Figure 1:
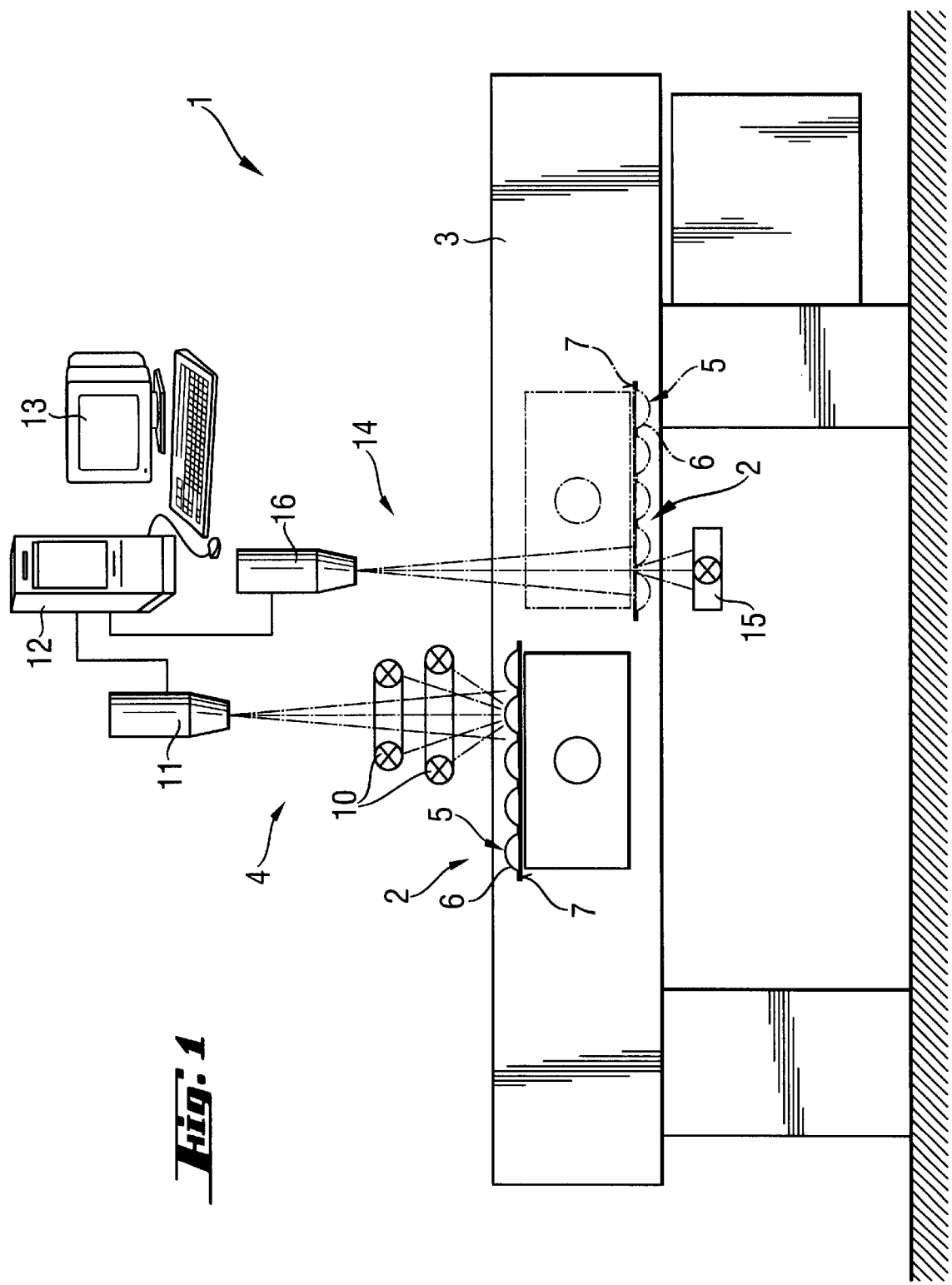
Figure 2:
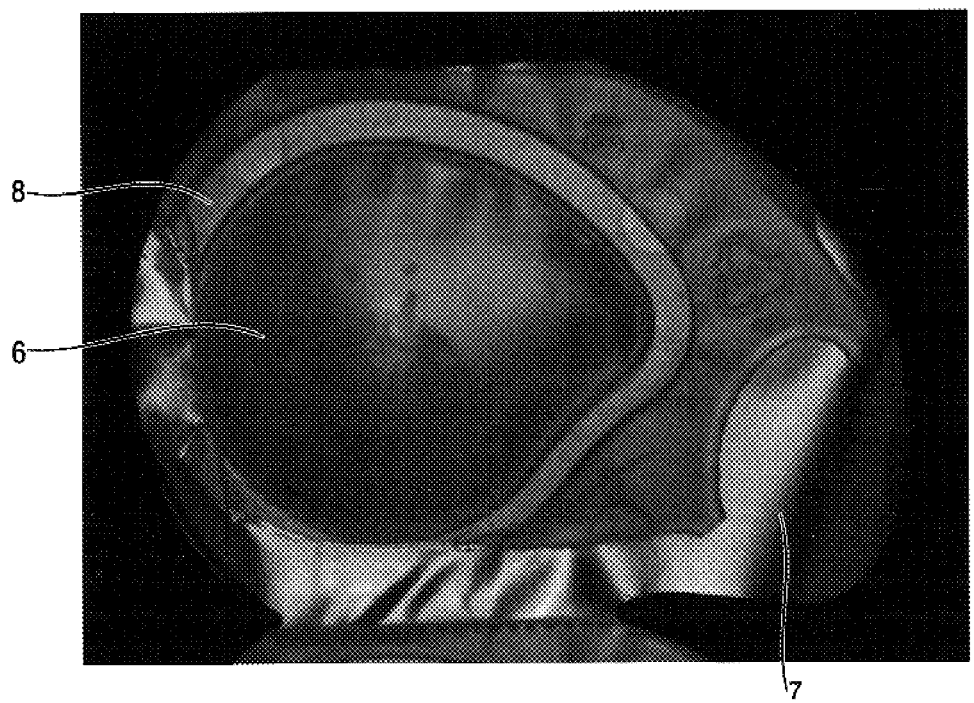
FIG. 2 shows an image of a damaged blister package being examined by an inspection device according to the invention.
Figure 3:
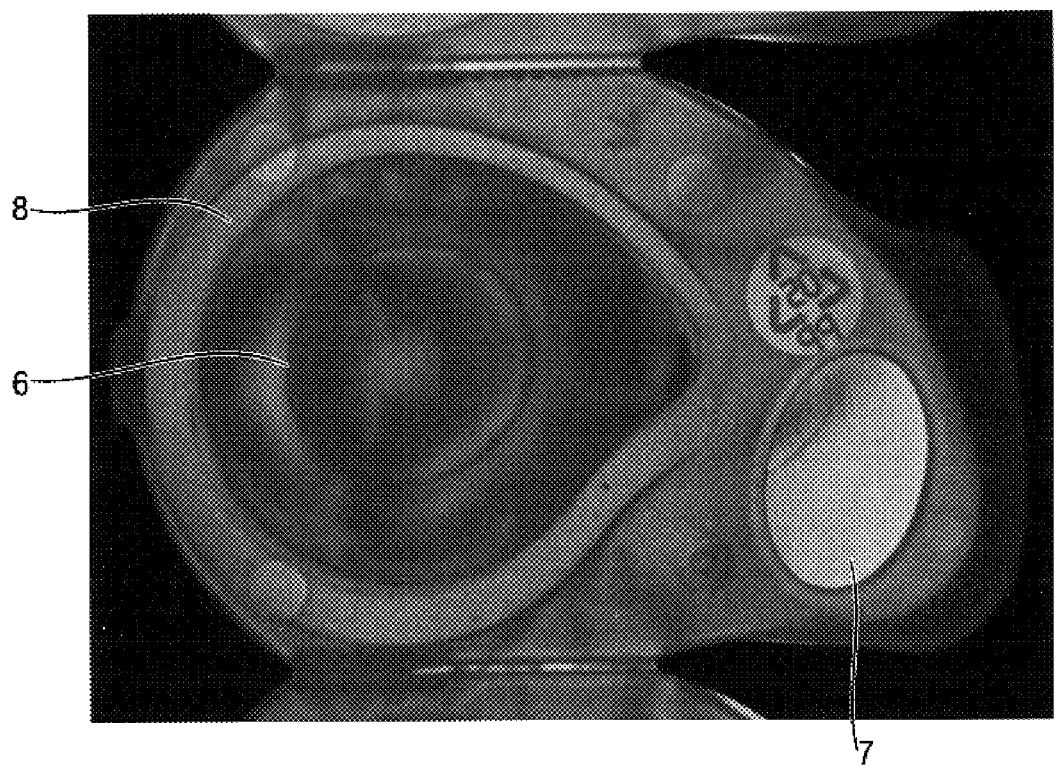
FIG. 3 shows an image of a blister package being examined, the sealing seam of which is open.
Figure 4:
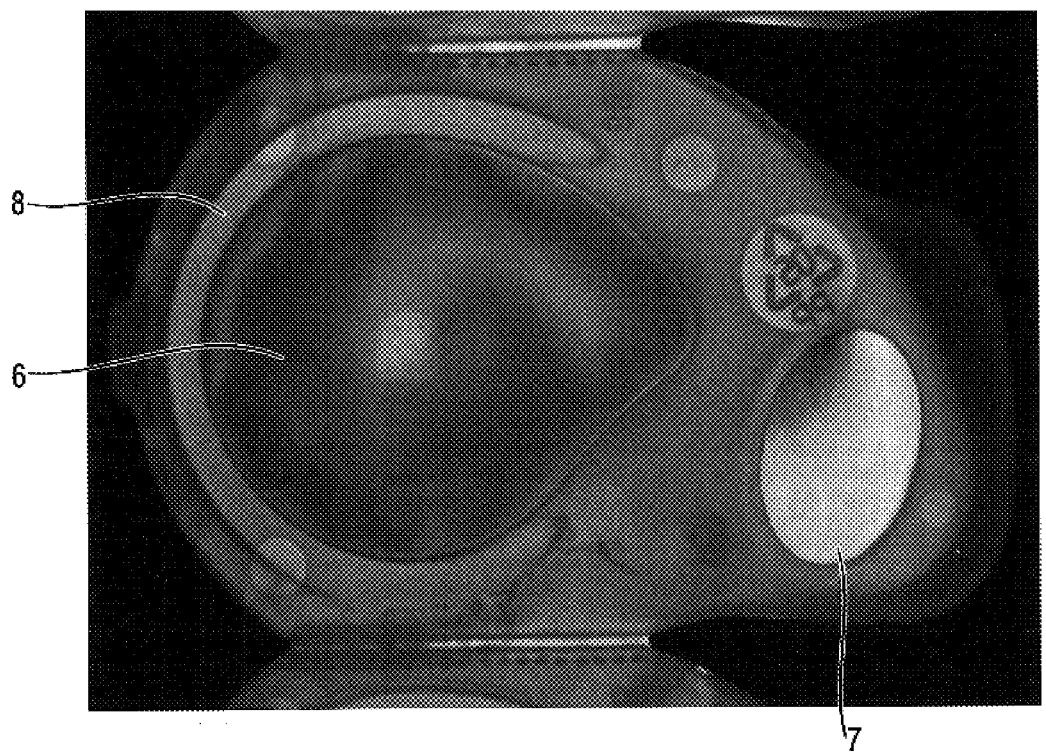
FIG. 4 shows an image of a blister package being examined, the sealing seam of which is open and which contains no saline.
Figure 5:
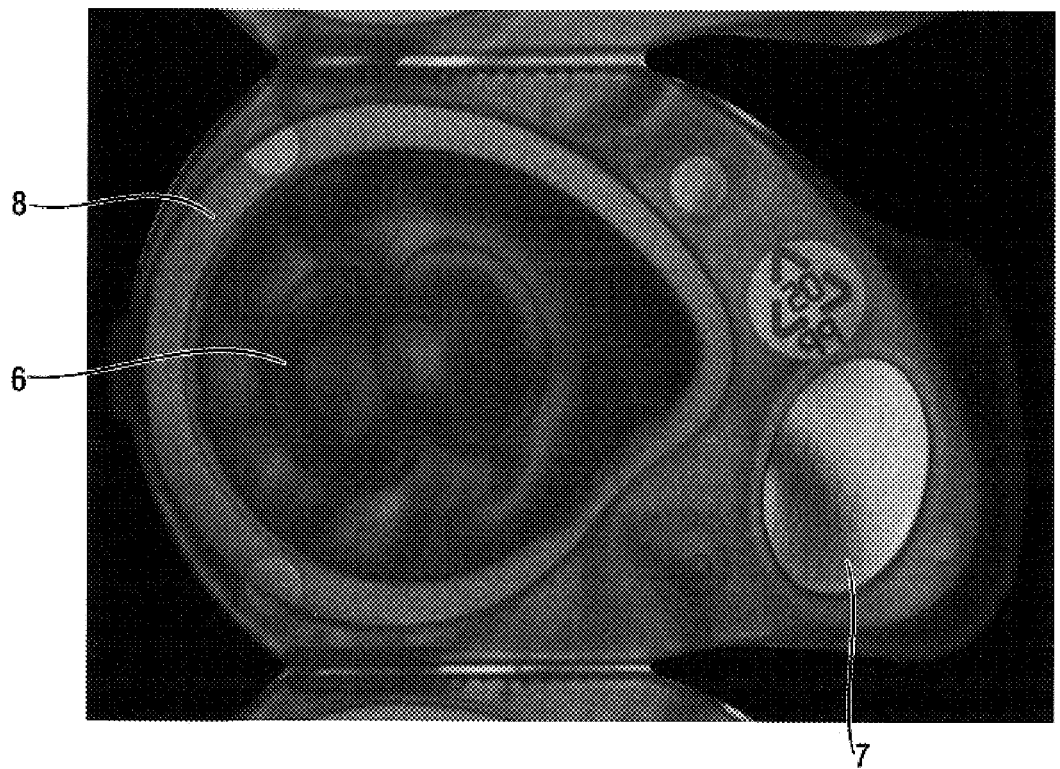
FIG. 5 shows an image of a blister package being examined, the sealing seam of which is too narrow.
Figure 6:
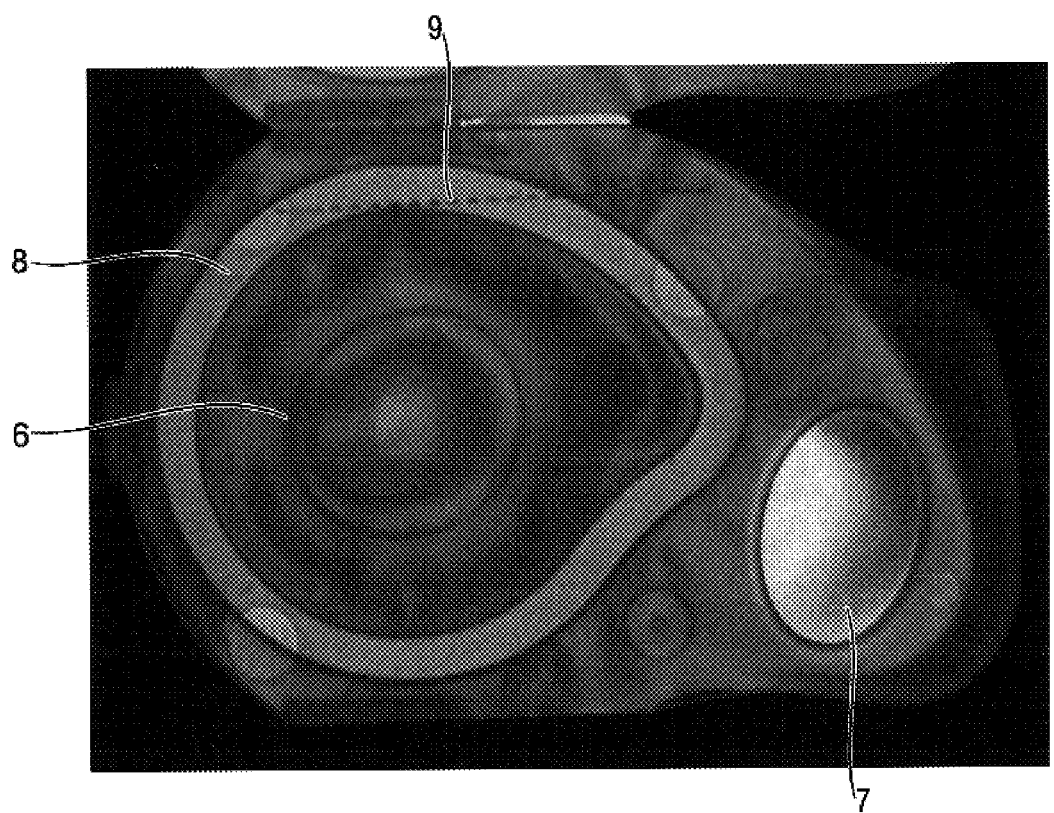
FIG. 6 shows an image of a blister package being examined in vertical light, in which the perforation line has shifted.

FIG. 1 illustrates an inspection device 1 for checking packages 2. The checking device advantageously consists of two units, whereby one unit includes the handling system 3 provided for transporting and preparing the packages 2 to be examined, and the other unit forms the image-recording and image-processing system 4 which carries out the actual recording and analysis of images. The image-processing system 4 is preferably of stationary design, and the handling system 3 transports the packages to be inspected under the image-recording system 4.

If the packages 2 are blister packages, they are preferably arranged in a blister strip 5. The blister strips 5 advantageously have five blister containers 6 arranged in series, which preferably consist of polypropylene. The blister containers 6 are connected to one another by a film strip 7, the shape of which corresponds to the contour of the upper side of the blister containers 6. Since the film strip 7 is sealed to the individual blister containers 6 along a sealing seam 8 after the object, preferably a contact lens, has been packaged, the blister containers 6 are thus joined together by the film strip 7. The film strip 7 is suitably provided with four perforation lines 9, which are preferably punched into the film strip 7 before it is applied to the blister containers 6. After the film strip 7 has been sealed to the blister containers 6, the perforation lines 9 should be arranged in the peripheral area between two touching blister containers 6, as a single blister container 6 can then be separated from the blister strip 5 by simply breaking it off.

The image processing system 4 preferably has at least two circular lights 10, which are advantageously arranged in an axis vertical to the suitably horizontal blister strips 5. The two circular lights 10 emit light preferably in a certain wavelength range in the visible spectrum, and the emission maxima of the two circular lights 10 are offset in relation to one other. It is appropriate for the emission maximum of one circular light to lie in the red range, while the emission maximum of the other circular light lies in the blue range, but they may be in any order. By arranging the two circular lights 10 having the same reflecting characteristic, each however emitting a different color, at two different heights, it is possible to illuminate the packages 2 to be examined evenly. By illuminating with colors, it is possible to have color classification in addition to the traditional methods, so that defective structures can be recognized more clearly and more quickly than with conventional grey value processing. To test the saline, the sealing seam 8 and the blister containers 6 for impurities, flaws and breaks, the blister strips 5 are firstly rotated by the handling system 3 using grippers or a suction assembly, so that the film 7 lies on the side facing away from the illuminating device 10. Since the blister containers 6 are of transparent construction, and contact lenses contained therein are likewise transparent, the light is reflected from the opaque blister film 7. A 3Chip-CCD color camera 11, preferably with 730×540 pixels, is advantageously used to receive the light reflected from the blister film 7. The CCD camera is linked to a computer 12, so that the colored image of the blister packages 2 is visible on a screen 13 and can be evaluated by an automatic image processing system. The images of different blister packages 2 may also be stored, so that statistical information about the appearance of various types of defects can be given. When the images are received, there is advantageously a provision for each individual blister container 6 of a blister strip 5 to be observed separately, so that five individual images are taken per blister strip 5. Testing of a blister strip 5 takes place in a maximum of 2.5 seconds, so that a rapid throughput is made possible. Using the image processing system, preferably the following defects are observed: flaws, breaks, missing blister container, particles in the sealing seam, width of the sealing seam, defective seal and break in the seal, missing perforation, position of the perforation, strength of the perforation, presence of saline.

Moreover, to observe the perforation lines 9, an additional image-receiving device 14 is advantageously provided. In this, the blister strips 5 are observed in transmitted light. To this end, an additional illumination device 15 is provided, which preferably emits white light. For technical reasons relating to the apparatus, this illumination device 15 is preferably arranged below the preferably horizontal blister strips 5. To observe the perforation lines 9 better, the blister strips 5 are rotated by 180° using grippers or a suction assembly, so that the film strip 7 again lies on the side facing away from the illumination device 15. Since the perforation lines 9 are observed in transmitted light, a second camera 16 is provided opposite the illumination device 14. Because of the clear light-dark image, it is possible to assess the perforation lines 9 exactly and with certainty. The distance between the camera 11 for the blister inspection and the camera 16 for the perforation inspection is advantageously ca. 135 mm. The camera 16 is also preferably linked to computer 12.

The accuracy of positioning the blister strips 5 in front of the two cameras 11, 16 should be preferably at least +/−0.5 mm in all directions. Deviations from the horizontal position impair the reproduction of the contour of the seal. If the deviation from the horizontal is greater than 3°, the reliability of the inspection is impaired, and if the deviation is greater than 5°, reliable inspection can no longer be guaranteed. The blister strips 5 should each remain still for the time it takes to take a picture, which is ca. 40 msec. The residual oscillation of the grippers and suction assembly of the handling system 3 should not exceed an amplitude of preferably 20 micrometers while the picture is being taken. Furthermore, there are suitable provisions for the system to be stopped automatically at any time, in order to be able to inspect an individual unit more closely. In addition, a type of operation should enable the inspection device to stop automatically at any observed defect.

The software structure is advantageously of a modular concept. This is to enable or simplify the implementation of improved algorithms or of new defect features which are unknown at the present time. Furthermore, the parameters for the preprocessing of images and for classification may be conveniently amended.

The inspection data preferably contain the following details:

test date and time lot number (batch)

depot number test position of the individual blister container or perforation test result: good or defective number, location and size of the recognized defective objects A statistical evaluation is conveniently undertaken for each depot, the following being evaluated: the number of tested packages, the number and percentage of each type of defect, the number and percentage of good lenses, the number of defective blister strips, and the number of defect-free blister strips.

FIGS. 2 to 6 illustrate images in black and white of spoiled blister packages. As explained, the containers were illuminated with two different colors from two different directions and then recorded by a 3CCD-Chip camera with 730×540 pixels. In particular, in the colored images not reproduced here, contours especially of the sealing seam, defects within and in the transition of the sealing seam, displacement of the film and cracks in the container are clearly visible. All the images were made in vertical light with a view onto the container.

Figure 7:
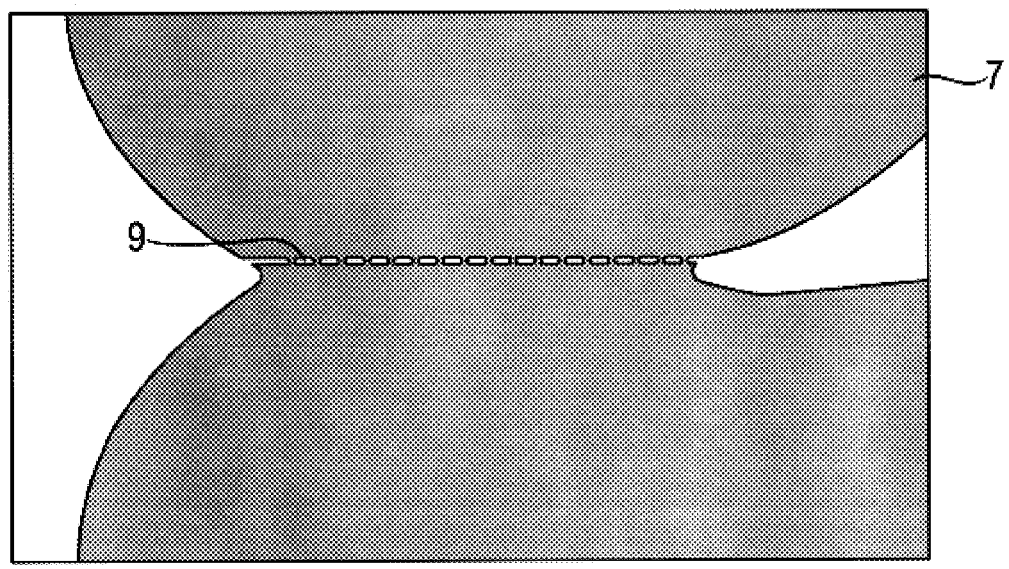
FIG. 7 shows a drawed reproduction of a blister package being examined in transmitted light, in which the perforation line is in the correct position.
Figure 8:
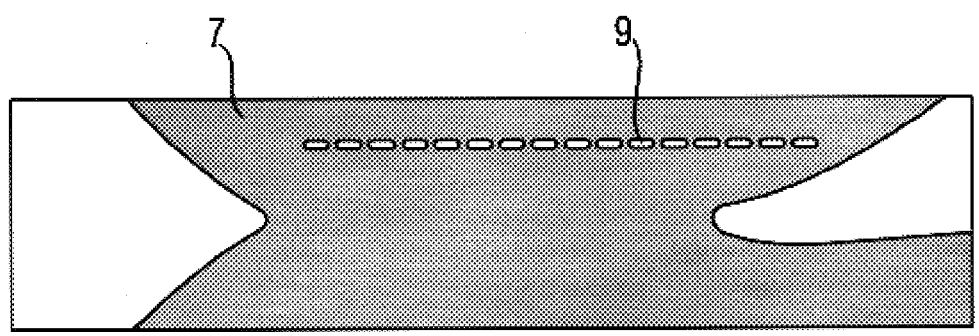
FIG. 8 shows a drawed reproduction of of a blister package being examined in transmitted light, in which the perforation line has shifted.

Although the perforation lines 9 form an image in vertical light, they are not so easy to evaluate. In contrast, there are no problems when operating in transmitted light. FIGS. 7 and 8 show images of perforation lines which were illuminated in transmitted light. The perforation lines 9 can be clearly recognized, and likewise the deviation of their position from the centre line between two blister containers 6.

Over all, the invention provides the possibility of inspecting packages, especially blister packages, without touching them, to check for defects such as flaws, breaks, missing blister container, particles in the sealing seam, width of the sealing seam, defective seal and break in the seal, missing perforation, position of the perforation, strength of the perforation, presence of saline. In addition, the defective packages can be sorted easily according to the results of the inspection.

We claim:

1. An automatic inspection device for inspecting packages comprising:

an image-receiving/processing system and a handling system for transporting and preparing packages to be examined in and out an inspecting position in the image-receiving/processing system, wherein the image-receiving/processing system comprises a camera and at least two light sources, wherein both the light sources have the same reflecting characteristics and each emits a light, wherein the emission maxima of two lights emitted from the two light sources are offset in relation to each other so that the two lights have different colors, wherein the two light sources are arranged opposite to a package to be inspected at a certain distance from one another in a way so that the package is illuminated vertically by both the light sources, and wherein the camera records two images with different colors by capturing lights reflected by the packages and transfers the two images to a computer for automatic image processing evaluation.

2. The device of claim 1, wherein at least one of said lights are circular.

3. The device of claim 1, wherein one light source has its emission maximum in the red wavelength range, and the other light source has its emission maximum in the blue wavelength range.

4. The device of claim 1, wherein said camera is a CCD camera.

5. A method for inspecting packages comprising:

under control of a computer, transporting and preparing a blister strip in and out an inspecting position;

illuminating vertically each package in the blister strip with each of at least two light sources, wherein both the light sources have the same reflecting characteristics and each emits a light, wherein the emission maxima of two lights emitted from the two light sources are offset in relation to each other so that the two lights have different colors;

wherein the two light sources are arranged opposite to a package to be inspected at a certain distance from one another in way so that the package is illuminated vertically by both light sources;

capturing lights reflected from each package in the blister strip by a camera to obtain two images with different colors;

transferring the two images to a computer for automatic image processing evaluation.

6. The device of claim 1, wherein said package to be inspected is a transparent blister container having a top which is sealed with a film.

7. The device of claim 6, wherein at least two blister containers are sealed by a film strip and form a blister strip, wherein the film strip has a perforation line at each point where two blister containers meet.

8. The device of claim 7, wherein the blister strip is arranged in relation to the illumination device in a manner allowing light to shine through each blister container and then be reflected by the film strip.

9. The device of claim 1, wherein at least one additional illumination device is provided to inspect the perforation lines of a blister pack.

10. The device of claim 9, wherein an additional camera receives light from the additional illumination device.

11. The device of claim 9, wherein the additional illumination device has a circular light.

12. The device of claim 11, wherein the circular light source emits white light.

13. The device of claim 4, wherein the camera is linked to the computer.

14. The method of claim 5, wherein at least one of said lights are circular.

15. The method of claim 5, wherein the camera is a CCD camera linked to the computer.

* * * * *